(12) United States Patent
Sullivan (10) Patent No.: US 7,041,075 B2
(45) Date of Patent: May 9, 2006

(54) ORTHOTIC FOOT DEVICES FOR BARE FEET AND METHODS FOR STABILIZING FEET

(76) Inventor: James Sullivan, 6 Anvil Dr., Cumberland, RI (US) 02864

( * ) Notice: Subject to any disclaimer, the term of this patent is extended or adjusted under 35 U.S.C. 154(b) by 244 days.

(21) Appl. No.: 10/703,009

(22) Filed: Nov. 6, 2003

(65) Prior Publication Data
US 2004/0102726 A1  May 27, 2004

Related U.S. Application Data

(60) Provisional application No. 60/429,582, filed on Nov. 27, 2002.

(51) Int. Cl.
*A61F 5/00* (2006.01)

(52) U.S. Cl. .............. 602/23; 602/28; 602/66; 602/5

(58) Field of Classification Search .......... 602/23, 602/28, 29, 66; 36/42, 34 A, 43, 145, 149, 36/140; D24/192; D2/961, 964
See application file for complete search history.

(56) References Cited

U.S. PATENT DOCUMENTS

| | | | | |
|---|---|---|---|---|
| 1,701,269 A * | 2/1929 | May | .................. | 602/66 |
| 1,788,852 A | 1/1931 | Arthur | | |
| 1,930,188 A | 10/1933 | Arthur | .................. | 128/166.5 |
| 2,237,652 A | 4/1941 | Capezio | .................. | 36/8.3 |
| 2,255,100 A | 9/1941 | Brady | .................. | 36/71 |
| 3,584,622 A * | 6/1971 | Domenico | .................. | 602/65 |
| 3,757,435 A | 9/1973 | Schwartz | .................. | 36/30 R |
| 3,861,398 A | 1/1975 | Leydecker | .................. | 128/615 |
| 4,188,736 A | 2/1980 | Keller | .................. | 36/80 |
| 4,227,321 A * | 10/1980 | Kling et al. | .................. | 36/91 |
| 4,360,027 A | 11/1982 | Friedlander et al. | .................. | 128/581 |
| 4,476,858 A | 10/1984 | Curtis | .................. | 128/80 R |
| 4,612,713 A | 9/1986 | Brown | .................. | 36/44 |
| 4,747,410 A | 5/1988 | Cohen | .................. | 128/581 |
| 4,887,368 A * | 12/1989 | Latzke | .................. | 607/111 |
| 4,888,225 A * | 12/1989 | Sandvig et al. | .................. | 428/71 |
| 5,036,851 A | 8/1991 | Cohen | .................. | 128/602 |
| 5,058,585 A | 10/1991 | Kendall et al. | .................. | 128/581 |
| D347,315 S | 5/1994 | Sell, Jr. et al. | .................. | D2/961 |
| D357,349 S | 4/1995 | Vasyli | .................. | D2/961 |
| D402,036 S | 12/1998 | Parsley et al. | .................. | D24/192 |
| 5,933,984 A * | 8/1999 | Carlson et al. | .................. | 36/43 |
| D420,784 S | 2/2000 | Riecken | .................. | D2/913 |
| 6,026,599 A * | 2/2000 | Blackwell et al. | .................. | 36/140 |
| 6,038,793 A * | 3/2000 | Kendall | .................. | 36/173 |
| 6,192,607 B1 * | 2/2001 | Kolada et al. | .................. | 36/145 |
| 6,460,275 B1 | 10/2002 | Bennett et al. | .................. | 36/144 |
| 6,502,330 B1 * | 1/2003 | David et al. | .................. | 36/88 |
| 6,558,339 B1 * | 5/2003 | Graham | .................. | 602/66 |

FOREIGN PATENT DOCUMENTS

DE  875 466  7/1949

OTHER PUBLICATIONS

PTO 05-6046; Schreiber Translations, Inc., INSOLE- Translation of DE 875,466.*

* cited by examiner

*Primary Examiner*—Henry Bennett
*Assistant Examiner*—Amanda Wieker
(74) *Attorney, Agent, or Firm*—Barlow, Josephs & Holmes, Ltd.

(57) ABSTRACT

An orthotic foot device that can be fastened to a person's bare foot is provided. The orthotic has a U-shaped hindfoot supporting region and an arched midfoot supporting region. A method for stabilizing and supporting a bare foot with the orthotic is also provided. The orthotic can be taped to a bare foot so that the foot is held in a neutral position upon foot impact. The orthotic is particularly suitable for bare foot athletes such as dancers and gymnasts.

12 Claims, 8 Drawing Sheets

ORTHOTIC FOOT DEVICES FOR BARE FEET AND METHODS FOR STABILIZING FEET

CROSS-REFERENCE TO RELATED APPLICATIONS

This application claims the benefit of U.S. Provisional Patent Application 60/429,582 having a filing date of Nov. 27, 2002, the entire contents of which are hereby incorporated by reference.

BACKGROUND OF THE INVENTION

The present invention relates generally to orthotic foot devices. Particularly, this invention relates to orthotic foot devices for bare feet. The invention also encompasses a method for stabilizing and supporting a bare foot by fastening the orthotic foot device to the foot.

In general, orthotics are appliances that provide a support or brace for the foot. Conventional orthotic foot devices are in the form of removable inserts that are placed inside a shoe. Some shoe inserts extend along only a portion of the foot, for example, from the heel to the ball of the foot. These partial inserts can provide some support, but tend to have a loose fit and often slip inside the shoe. Other shoe inserts extend along the entire length of the foot and are less likely to slip. However, these full-length inserts are bulky and can crowd the anterior portion of the shoe. Still other shoe inserts are affixed to the interior of the shoe by an adhesive such as glue. Shoe inserts can be made from a variety of materials. For example, flexible materials such as elastomers, or rigid materials such as hard plastics and rubbers can be used. Such conventional shoe inserts include, U-shaped heel pads, arch supports, cups that encompass the heel and midfoot, and rubber metatarsal pads.

The foot absorbs tremendous forces when engaging in a weight-bearing activity such as walking, running, or jumping. Typically, when a person walks or runs, the outer part of his/her heel strikes the ground first with the foot in a supinated position. As the person transfers his/her weight to the inside portion of the foot, the arch of the foot is flattened, and the foot rolls inward to a pronated position. Then a person pushes off on the ball of his/her foot, and the foot rolls outward again. These continuous stresses on the outer and inner portions of the foot can cause ligaments, tendons, and muscles in the foot to sprain or tear. Placing a conventional orthotic foot device inside the shoe helps to control motion of the foot during the gait cycle within a prescribed parameter. When running or walking, the foot and orthotic device work in synergy to control motion within the foot during the gait cycle.

Various orthotic foot devices that are designed for altering a person's gait cycle or controlling gait motion are known in the art. For example, Kendall et al., U.S. Pat. No. 5,058,585 discloses an orthotic shoe insert having a heel portion for engaging the sides of the heel, a middle portion for engaging the medial portion of the foot, and a front portion for engaging the forefoot. The heel portion is described as being a substantially U-shaped wedge for minimizing the heel eversion component of pronation. The middle portion is also shaped as a wedge and functions to support the arch of the foot. The front portion extends to the first and second metatarsal heads of the foot and slightly elevates these joints so that there is greater control of pronation. According to the '585 Patent, the orthotic works synergistically with the design of the shoe to provide proper orientation of the foot during the gait cycle.

Friedlander et al., U.S. Pat. No. 4,360,027 discloses an orthotic device for inserting into shoes. The orthotic includes a posted therapeutic portion and a cut-out, non-posted, non-therapeutic portion. Particularly, the orthotic comprises a U-shaped heel-supporting region, a medial arch-supporting region, and a forefoot-supporting region. The toe-receiving (forefoot) supporting region supports the metatarsalphalangeal joint. According to the '027 Patent, each supporting region is constructed with appropriate posting to prevent excessive pronation during the gait cycle.

Although some conventional orthotic shoe inserts may provide some support and prevent some foot injuries, these devices are designed for use with shoes or sneakers. The orthotic insert works with the shoe or sneaker to control foot motion in gait. Such shoe inserts are not designed for bare foot athletes such as dancers and gymnasts. These bare foot athletes must tape their feet and ankles to provide ligament support and stability, but taping, by itself, is often insufficient. Thus, an orthotic foot device specially designed for a bare foot athlete is needed.

The bare foot athlete should be able to use such an orthotic without any other footwear such as shoes, sneakers, or the like. In addition, the orthotic should be lightweight and provide good bracing and support to the rear and midfoot aspects of the bare foot upon foot impact. Further, the orthotic should be capable of holding the foot in a neutral position and keeping the center of pressure centrally beneath the foot upon impact without concern for the gait cycle as in contrast to other orthotics.

The present invention provides such an orthotic foot device. Further, the present invention provides a method for stabilizing and supporting a bare foot by fastening the orthotic to the foot using tape or other suitable adhesive means. These and other objects, features, and advantages of this invention are evident from the following description and attached figures.

SUMMARY OF THE INVENTION

The present invention relates to an orthotic foot device for supporting a person's bare foot. The J-shaped orthotic comprises: a) a hook segment (U-shaped) hindfoot supporting region having a medial segment connected to a lateral segment that defines an open space therebetween for the plantar aspect of the heel, and b) an arched midfoot supporting region extending from the hindfoot region. The medial and lateral segments of the hindfoot supporting region are adapted for supporting the medial and lateral sides of a person's heel. The midfoot supporting region has a medial portion and lateral portion adapted for supporting the plantar aspect of the midfoot and maintaining the midfoot in its neutral position. The orthotic can be made from any suitable rigid or semi rigid material such as a plastic. Composite plastic compositions containing reinforcing materials may be used.

The invention also includes a method for supporting a bare foot comprising the step of fastening the orthotic to a bare foot with tape or other suitable adhesive means so that the orthotic contacts the plantar aspect of the foot. The adhesive tape can be wrapped around the orthotic and foot. The fastened orthotic supports the foot so that the foot is held in a neutral position upon foot impact. The fastened orthotic decreases deformation of the musculoskeletal structures upon landing and impact forces.

BRIEF DESCRIPTION OF THE DRAWINGS

The novel features that are characteristic of the present invention are set forth in the appended claims. However, the preferred embodiments of the invention, together with further objects and attendant advantages, are best understood by reference to the following detailed description taken in connection with the accompanying drawings in which:

DETAILED DESCRIPTION OF THE PREFERRED EMBODIMENTS

The orthotic foot device of the present invention is an integrated article comprising supporting regions for the hindfoot and midfoot. Basically, the anatomy of the foot can be divided into three bony regions. The hindfoot region generally includes the ankle (talus) and heel (calcaneus) bones. The midfoot region includes the cuboid, cuneiform, and navicular bones that form the longitudinal arch of the foot. The forefoot region includes the metatarsals and the toes. There are several important joints that allow the foot to move in various directions including the subtalar joint; calcaneal-cuboid joint; talo-navicular joint; navicular-cuneiform joints; and lisfrancs (tarsal-metatarsal) joint.

Figure 1:
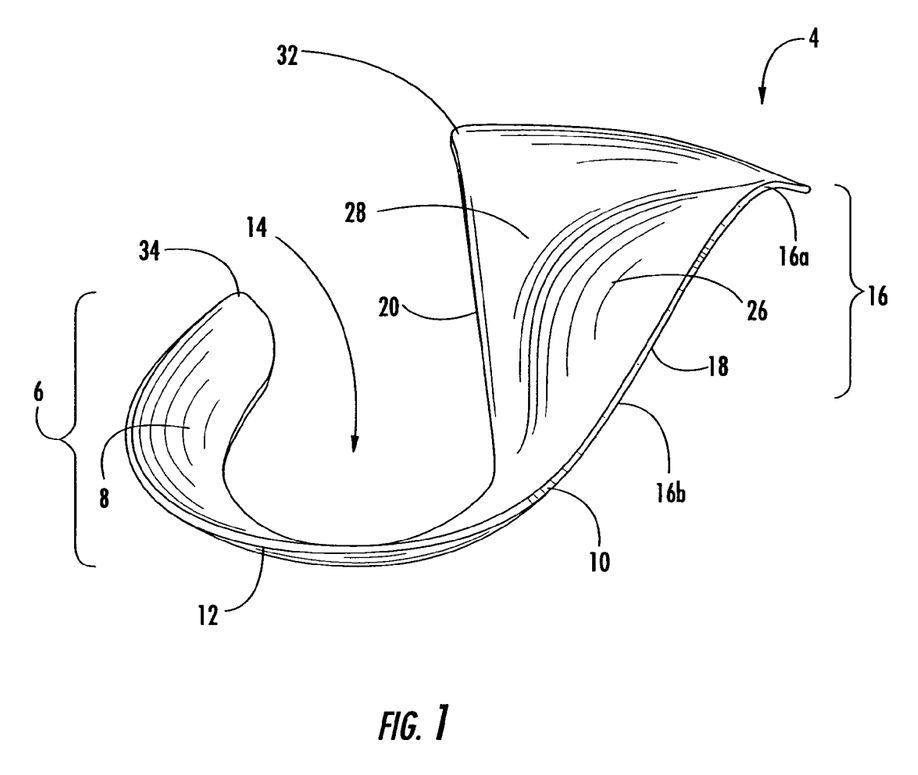
FIG. 1 is a perspective view of the orthotic device of the present invention used for bracing a person's left bare foot.

Referring to FIG. 1, one embodiment of the "J-shaped" orthotic foot device 4 of this invention is shown. The orthotic device 4 shown in FIG. 1 can be used to support a person's left bare foot in accordance with this invention. (The orthotic device 4A shown in FIG. 4 can be used to support a person's right bare foot.)

Figure 4:
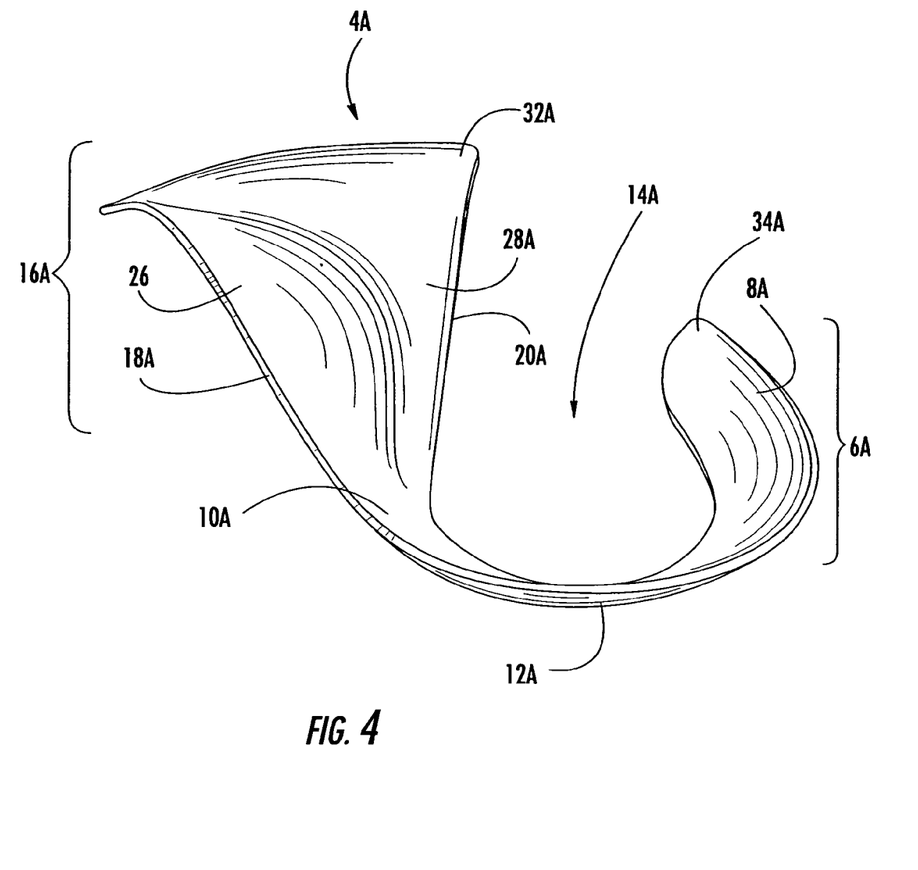
FIG. 4 is a perspective view of the orthotic device of the present invention used for bracing a person's right bare foot.

The orthotic 4 has a substantially "U-shaped" hindfoot region 6 for supporting the hindfoot. As discussed in further detail below, the hindfoot region has no external posting mounted thereon, because the orthotic is not designed for adjusting a person's gait. The U-shaped hindfoot region 6 has a solid outer (lateral) segment 8 and inner (medial) segment 10 that are integrally connected by a solid curved segment 12. Since the hindfoot region 6 provides a brace for a person's heel, it will have about the same width as that person's heel. The lateral segment 8 and medial segment 10 are adapted for supporting the lateral and medial sides of a person's heel. In addition, the hindfoot region 6 includes an open portion 14, where the plantar aspect of the heel rests. This exposed section 14 allows a significant portion of the heel to be in direct contact with a surface upon foot impact. Furthermore, the orthotic devices of this invention 4 and 4A do not have supporting regions for the forefoot. Thus, the plantar aspect of the forefoot remains exposed and can directly contact a surface upon foot impact.

These open, non-supporting regions in the orthotic help make the orthotic desirable for bare foot athletes. For example, bare foot gymnasts can wear this orthotic and their heel and forefoot can maintain direct contact with the gym mat, balance beam, vault, or other piece of equipment. A gymnast's ability to touch and naturally feel the surface with his or her bare feet is important. Gymnasts want to have a true feel for the surface so that they can intuitively adjust their body mechanics and satisfactorily perform their routines.

Figure 2:
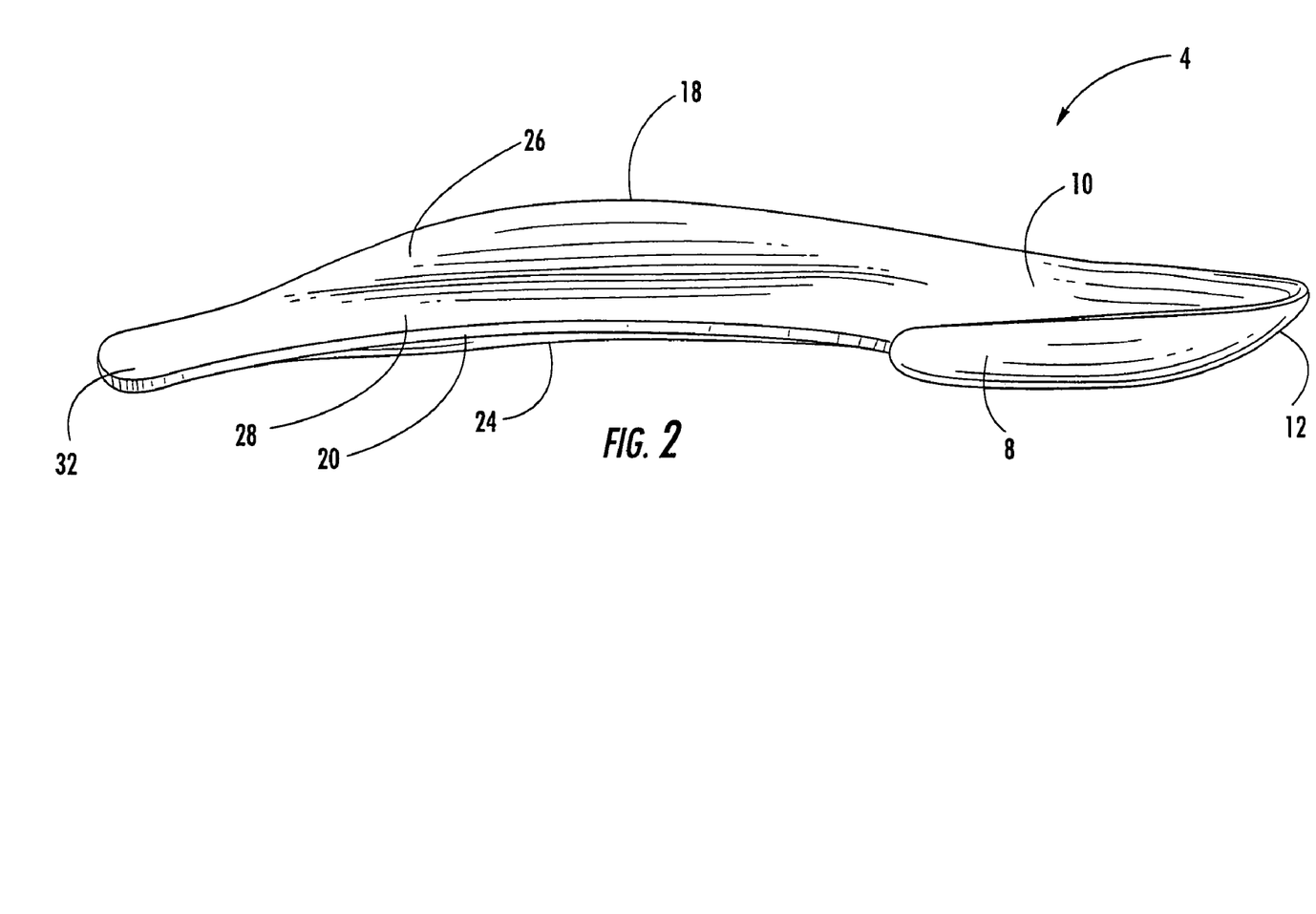
FIG. 2 is a side perspective view along the lateral edge of the orthotic device shown in FIG. 1.
Figure 3:
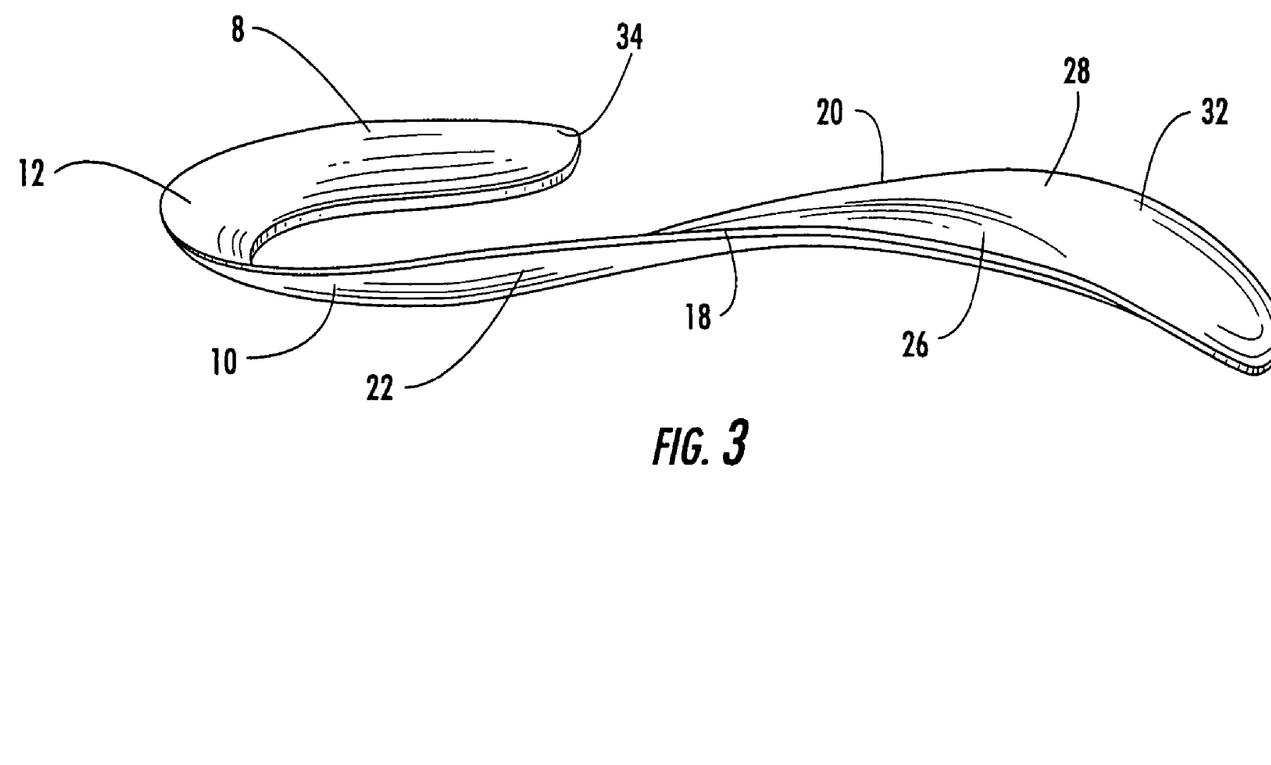
FIG. 3 is a side perspective view along the medial edge of the orthotic device shown in FIG. 1.

Referring back to FIG. 1, the arched midfoot supporting region 16 extends from the hindfoot supporting region 6 and provides a brace for the midfoot, particularly supporting the longitudinal arch of the foot (not shown). The arched midfoot region 16 includes an anterior portion 16a and a posterior portion 16b. Referring to the posterior portion 16b, the arch curves upwardly from the medial segment 10 of the hindfoot region 6 to a peak and then curves downwardly to the anterior portion 16a. The arched midfoot region 16 has a medial edge 18 and a lateral edge 20. As shown in FIGS. 2 and 3, the curved area 22 under the medial edge 18 is greater than the curved area 24 under the lateral edge 20. The medial portion 26 is substantially curved to support the medial side of the plantar aspect of the midfoot and maintain the neutral position of the foot upon impact. The lateral portion 28 is slightly curved to support the lateral side of the plantar aspect of the midfoot. Since more strain is placed on the medial side of the plantar aspect of the midfoot, where the longitudinal arch is more prominent, the medial side 26 of the orthotic has a greater curve height than the lateral side of the orthotic. Nevertheless, it is still important to provide some support to the lateral side of the plantar aspect of the midfoot to maintain the neutral position of the foot. Thus, the lateral side 28 of the orthotic is slightly curved to provide such support.

The anterior portion 16a of the midfoot region 16 is generally flat and relatively wide. As shown in FIG. 1, the anterior portion 16a further helps to support the lateral and medial sides of the plantar aspect of the midfoot. The corner edge 32 of the lateral side of the anterior portion 16a is generally in alignment with the outer corner edge 34 of the lateral segment 8 of the hindfoot region 6. Thus, the orthotic foot device of this invention is a fully supporting orthotic that provides support and stability equally to the lateral and medial sides of the plantar aspect of the foot and reduces foot movement upon impact.

Figure 5:
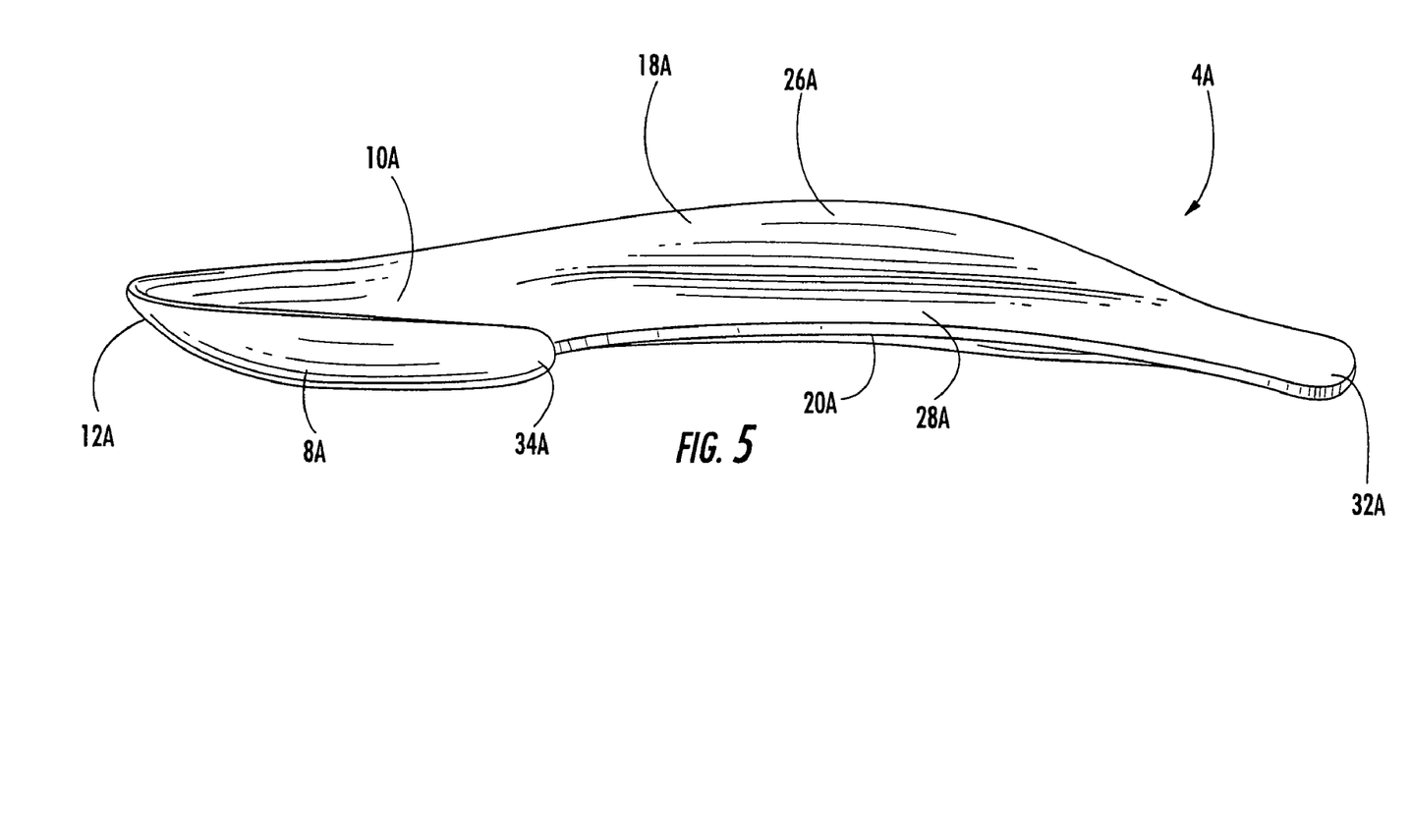
FIG. 5 is a side perspective view along the lateral edge of the orthotic device shown in FIG. 4.
Figure 6:
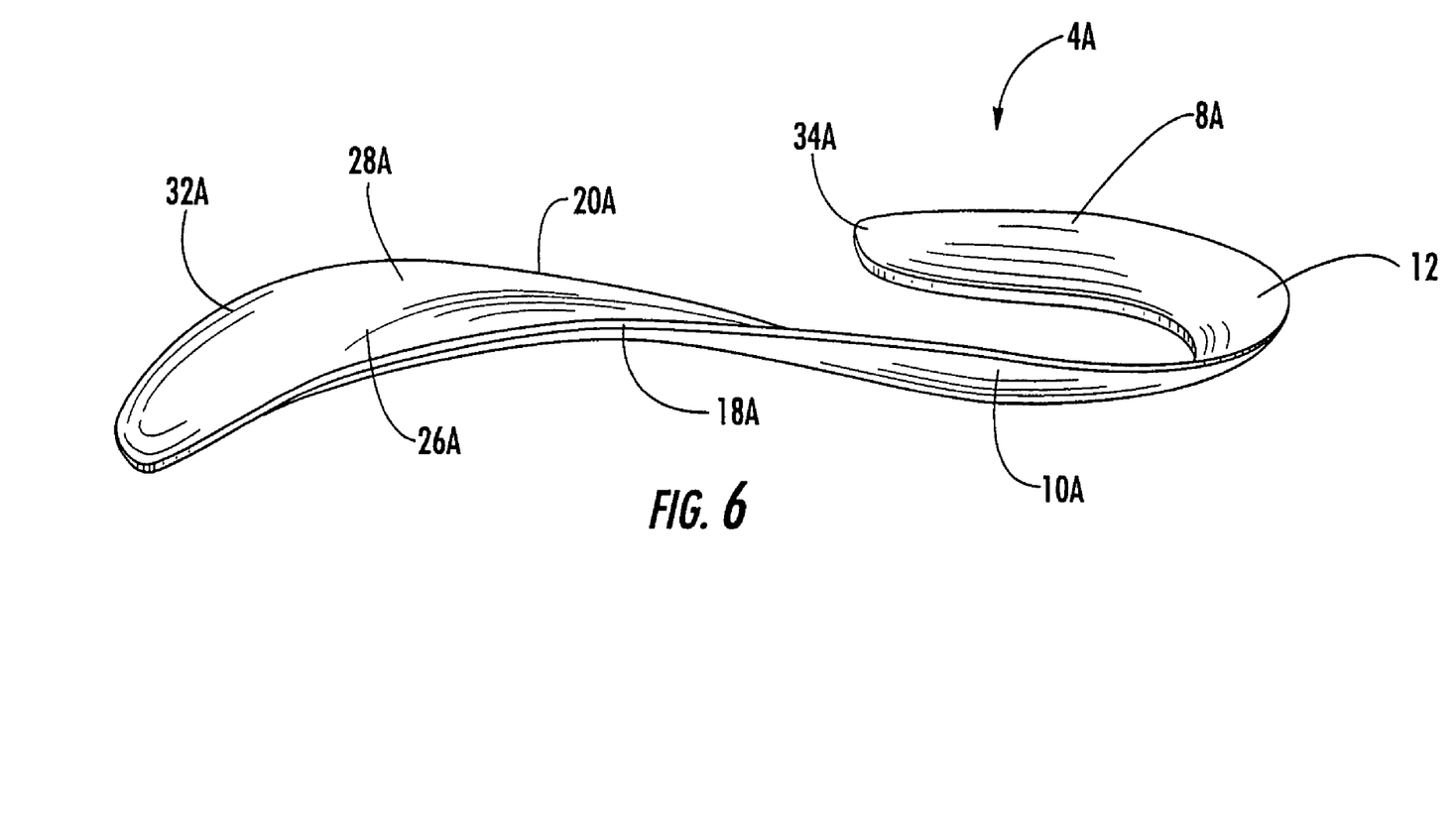
FIG. 6 is a side perspective view along the medial edge of the orthotic device shown in FIG. 4.

The orthotic foot device 4 shown in FIGS. 1–3 can be used for supporting a person's left bare foot. A corresponding, inverted "J-shaped" orthotic foot device 4A that is a mirror structure of the orthotic foot device 4 can be used for supporting a person's right bare foot as shown in FIGS. 4–6. The orthotic device 4A, designed for a person's right bare foot, comprises a U-shaped hindfoot region 6A having a lateral segment 8A connected to a medial segment 10A that defines an open space 14A therebetween, and an arched midfoot supporting region 16A extending from the hindfoot region 6A. The lateral 8A and medial 10A segments of the hindfoot region 6A support the lateral and medial sides of a person's heel. The arched midfoot region 16A has a lateral portion 20A and medial portion 18A for supporting the plantar aspect of the midfoot. FIG. 5 shows the lateral edge 20A of the orthotic 4A in more detail, and FIG. 6 shows the medial edge 18A of the orthotic 4A in more detail.

The orthotic foot device of this invention is lightweight and can be made from any suitable semi rigid or rigid material such as plastics, composite plastics, rubber, or the like. The orthotic device can be used for stabilizing and supporting a bare foot particularly the foot of a bare foot athlete as described in further detail below.

Figure 7:
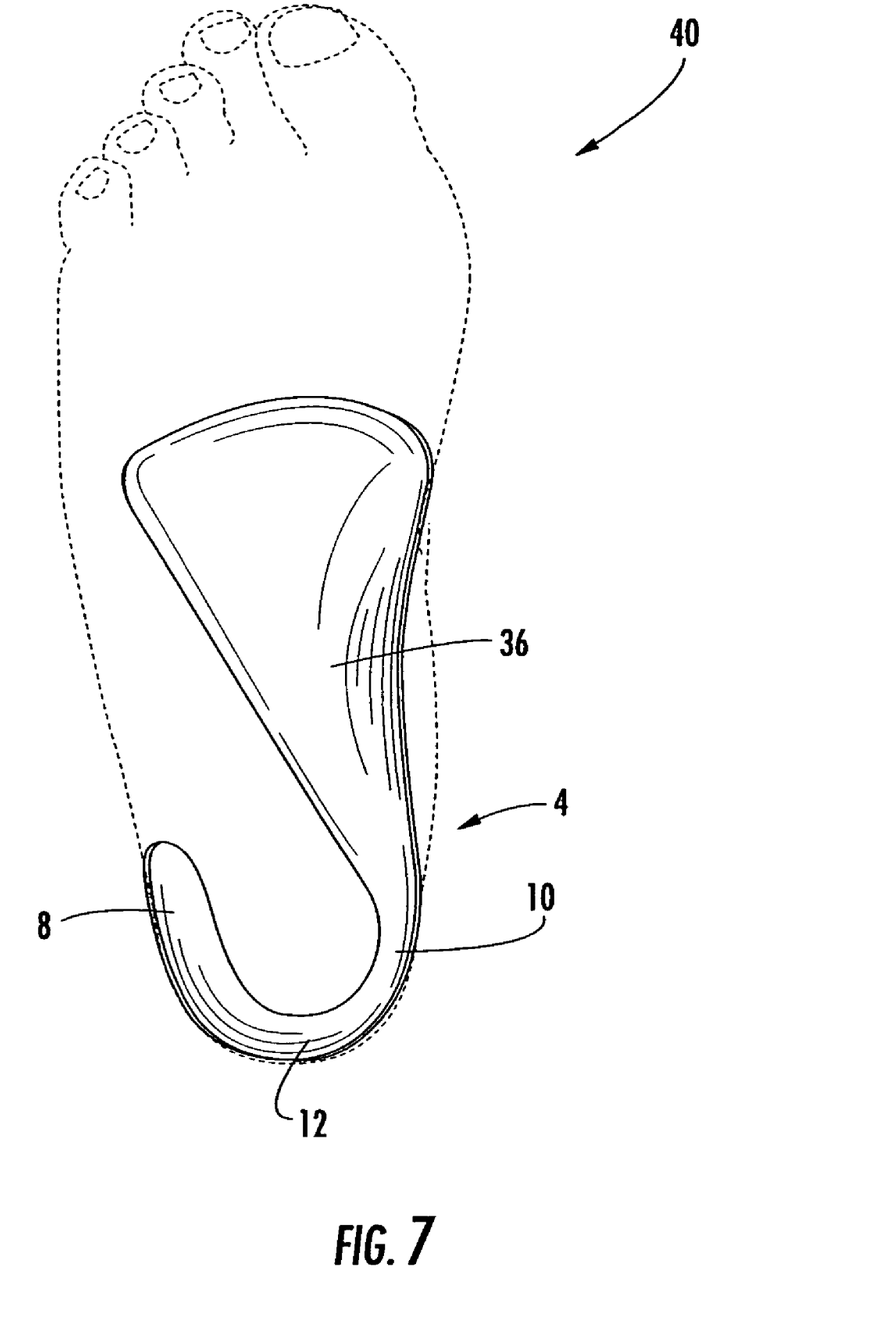
FIG. 7 is a cut-away view showing the orthotic device of FIG. 1 in contact with a person's left bare foot.

The orthotic foot devices 4 and 4A can be fastened to the left and right bare foot respectively using a suitable adhesive such as tape or elastic straps. Particularly, athletic foot/ankle tape can be used to secure the orthotic to the foot. Referring to FIG. 7, which shows a cut-away view of the left foot 40, the orthotic 4 includes an upper surface 36 that engages the plantar aspect of the foot and a lower surface 38 (not shown) that engages a floor or other surface that a person wearing the orthotic would contact while participating in a sport or other activity.

Figure 8:
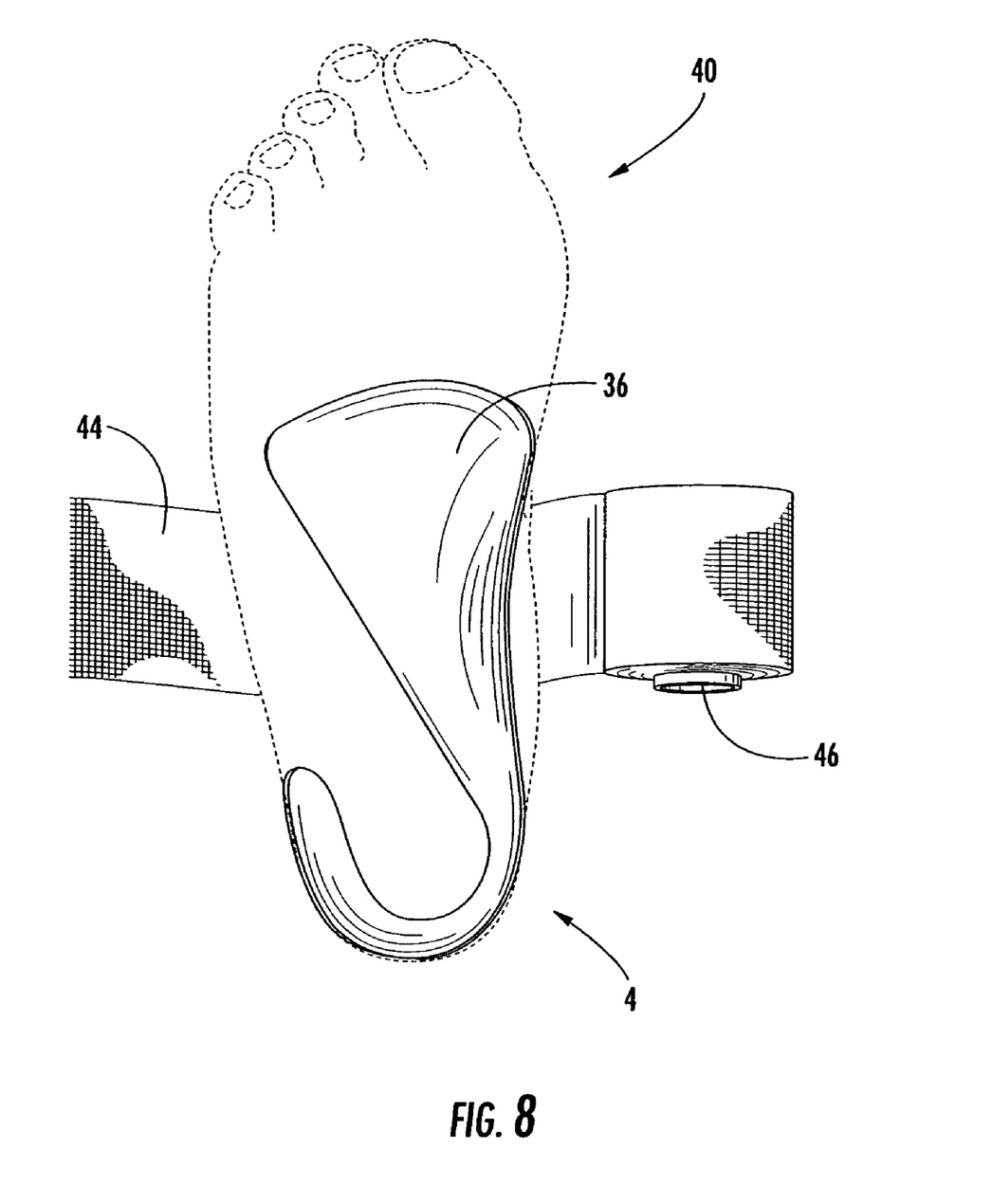
FIG. 8 is a cut-away view showing the orthotic device of FIG. 1 being fastened to a person's left bare foot with athletic tape.

Referring to FIG. 8, athletic tape 44 from a core roll 46 can be wrapped around the orthotic 4 and foot 40 beginning at the anterior portion of the foot. The tape 44 can be wrapped under the lower surface 38 (not shown) of the orthotic 4 and over the dorsal surface of the foot 40 following a taping path from the inside to the outside of the foot 40. The roll of tape 44 is wrapped continuously around the orthotic 4 and foot 40 so that each new layer of tape overlaps a portion of the previously wrapped layer of tape. Then, the tape 44 can be wrapped around the ankle if desired. The orthotic foot device 4A can be fastened to a person's right foot in a similar manner.

This taping method provides a stable brace or splint for the bare foot. The taping of the orthotic device to the bare foot provides support and stability to the medial and lateral sides of the plantar aspect of the foot. The taping may also help to stabilize the ligaments surrounding the ankle joint.

When the orthotic foot device of this invention is fastened to a bare foot using the method described above, the device acts as a splint providing excellent support and stability to the foot. Dancers, gymnasts, and other bare foot athletes can engage in vigorous running and jumping activities while the orthotic is held in position against the foot.

The orthotic foot device of this invention limits deformation of the foot upon impact by maintaining the center of pressure centrally beneath the foot. The taped orthotic holds the bare foot in a neutral position upon foot impact. Particularly, the orthotic acts as a brace or splint when taped to the foot and limits motion at the subtalar; calcaneal-cuboid joint; talo-navicular joint; navicular-cuneiform joint; and lisfrancs (tarsal-metatarsal) joint. The orthotic maintains support equally on the medial and lateral aspects of the foot, through all of the above joints, upon foot impact. However, the device does not limit forefoot motion. As discussed above, the plantar aspect of the forefoot is exposed so that it can be in direct contact with a surface upon foot impact.

Also, as discussed above, some conventional orthotic shoe inserts have a posting material mounted on their surfaces to control foot motion. The posting is added to the inner and/or outer edges of the orthotic shoe insert to help prevent excessive pronation or supination of the foot. However, in the orthotic foot device of this invention, external posting is not mounted on the orthotic, because the orthotic is not designed as a shoe insert for altering a person's gait cycle or controlling gait motion. Also, such external posting can interfere with a person naturally feeling a surface upon foot impact, and this natural feeling is important for bare foot athletes.

It is appreciated by those skilled in the art that various other changes and modifications can be made to the illustrated embodiments and description herein without departing from the spirit of the present invention. All such modifications and changes are intended to be covered by the appended claims.

What is claimed is:

1. An orthotic splint for providing stability and support to the lateral and medial sides of a bare foot during a bare foot activity, said orthotic splint comprising:

a U-shaped hind-foot portion having a lateral segment and a medial segment integrally connected by a central curved heel segment, said U-shaped hind-foot portion defining an open space for receiving a plantar aspect of a heel of said barefoot, and a mid-foot portion having a medial arch segment integrally connected to and extending forwardly from said medial segment of said hind-foot portion, and further having a lateral segment extending from said medial segment, said orthotic splint comprising a substantially rigid material and being configured and arranged as a unitary molded structure having an inner surface which is contoured to naturally conform to and engage the outside surfaces of the hind-foot and mid-foot regions of said bare foot, said orthotic splint further having an outer surface which is contoured to substantially conform to said inner surface, said orthotic splint having no external posting on said outer surface thereof, whereby said orthotic splint is placed in contact with said bare foot and secured directly to said bare foot with a wrapping material wrapped around said orthotic splint and said bare foot and worn during a bare foot activity to support said bare foot.

2. The orthotic splint of claim 1 wherein said medial arch segment of said midfoot portion has a greater curve height than said lateral segment of said midfoot portion.

3. The orthotic splint of claim 1 wherein the lateral and medial segments of the hind-foot portion are curved outwardly and upwardly to support the lateral and medial sides of the plantar aspect of the heel.

4. The orthotic splint of claim 1 wherein said mid-foot portion has an anterior area and a posterior area, the posterior area being substantially arched and the anterior area being substantially flat.

5. The orthotic splint of claim 1 wherein said splint is constructed from a plastic material.

6. The orthotic splint of claim 1 wherein said medial arch segment of said midfoot portion has a greater curve height than said lateral segment of said midfoot portion.

7. The orthotic splint of claim 1 wherein the lateral and medial segments of the hind-foot portion are curved outwardly and upwardly to support the lateral and medial sides of the plantar aspect of the heel.

8. The orthotic splint of claim 1 wherein said mid-foot portion has an anterior area and a posterior area, the posterior area being substantially arched and the anterior area being substantially flat.

9. The orthotic splint of claim 1 wherein said splint is constructed from a plastic material.

10. A method for providing stability and support to the lateral and medial sides of a bare foot during a bare foot activity, said method comprising the steps of:

providing an orthotic splint comprising:

a U-shaped hind-foot portion having a lateral segment and a medial segment integrally connected by a central curved heel segment, said U-shaped hind-foot portion defining an open space for receiving a plantar aspect of a heel of said barefoot, and a mid-foot portion having a medial arch segment integrally connected to and extending forwardly from said medial segment of said hind-foot portion, and further having a lateral segment extending from said medial segment, said orthotic splint comprising a substantially rigid material and being configured and arranged as a unitary molded structure having an inner surface which is contoured to naturally conform to and engage the outside surfaces of the hind-foot and mid-foot regions of said bare foot, said orthotic splint further having an outer surface which is contoured to substantially conform to said inner surface, said orthotic splint having no external posting on said outer surface thereof, placing said orthotic splint in contact with said bare foot; and securing said orthotic splint directly to said bare foot with a wrapping material wrapped around said orthotic splint and said bare foot, said orthotic splint being worn during a bare foot activity to support said bare foot.

11. The method of claim 10 wherein said wrapping material comprises an adhesive wrapping material.

12. The method of claim 11 wherein said wrapping material comprises an adhesive tape.

* * * * *